United States Patent [19]

Tsunoyama et al.

[11] Patent Number: 4,652,128
[45] Date of Patent: Mar. 24, 1987

[54] METHOD OF PERFORMING CONTINUOUS ON-LINE LASER EMISSION SPECTROSCOPIC ANALYSIS ON A FLOWING FLUID SAMPLE BY LASER AND APPARATUS THEREFOR

[75] Inventors: Kouzou Tsunoyama; Wataru Tanimoto, both of Chiba; Yoshiharu Ohashi, Setagaya; Shigeyuki Kimura, Hino; Fumio Asakawa, Hachiouji, all of Japan

[73] Assignees: Kawasaki Steel Corporation; Japan Spectroscopic Co., Ltd; Spectral Instrument Co., all of Japan

[21] Appl. No.: 681,436

[22] Filed: Dec. 13, 1984

[51] Int. Cl.$^4$ .................................. G01N 21/63
[52] U.S. Cl. .................................... 356/318
[58] Field of Search ............. 356/313, 317, 318, 417

[56] References Cited

U.S. PATENT DOCUMENTS 3,659,944  5/1972  Bojic ............................. 356/313
3,901,599  8/1975  Meric ............................ 356/318

OTHER PUBLICATIONS

Runge et al., "Spectrochemical Analysis of Molten Metal Using a Pulsed Laser Source", Spectrochimica Acta, vol. 22, Sep. 1966, pp. 1678–1680.

*Primary Examiner*—Vincent P. McGraw
*Attorney, Agent, or Firm*—Parkhurst & Oliff

[57] ABSTRACT

A focusing lens having a focal length f is provided at a position spaced a distance L apart from a substance to be measured in the fluid state, the relationship between L and f is controlled, so that the formula:

$$0.95f \leq L \leq 1.05f$$

is constantly satisfied, and the light emitted when a high output pulse laser irradiates the surface of the substance to be measured is analyzed spectroscopically so that the influence of variations on the surface of the substance to be measured can be avoided and a stabilized laser emission spectroscopically analysis on-line can be conducted as the substance to be measured flows.

9 Claims, 5 Drawing Figures

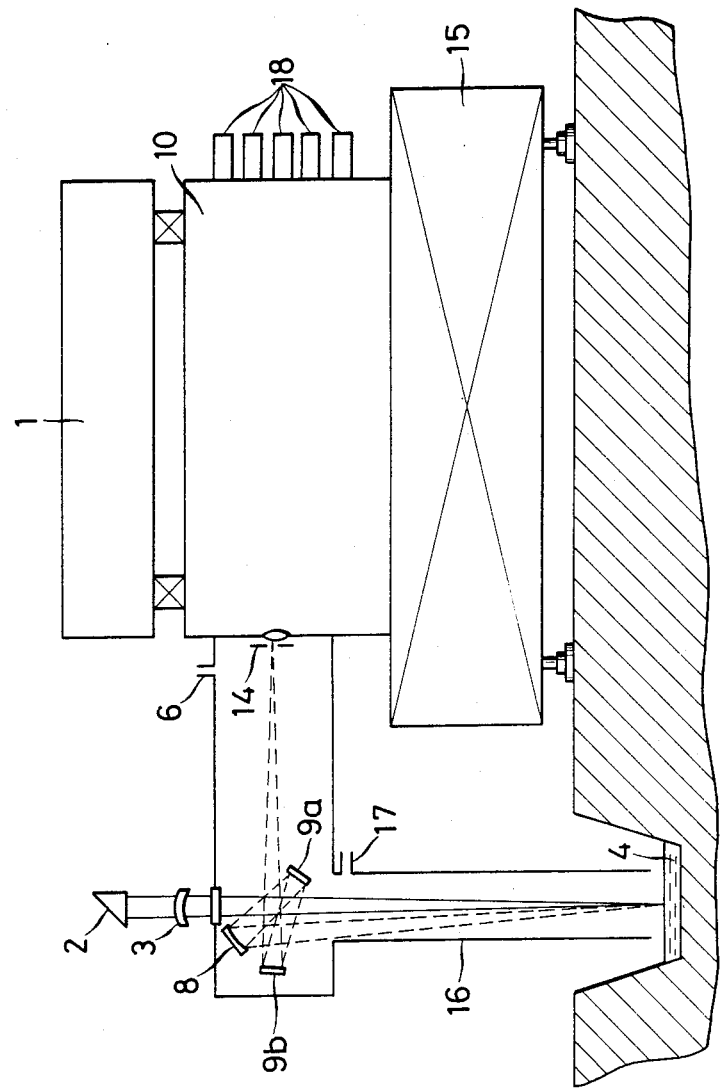

METHOD OF PERFORMING CONTINUOUS ON-LINE LASER EMISSION SPECTROSCOPIC ANALYSIS ON A FLOWING FLUID SAMPLE BY LASER AND APPARATUS THEREFOR

BACKGROUND OF THE INVENTION

1. Field of the Invention

This invention relates to a method of performing continuous on-line analysis by laser of multiple constituent elements of a metal or an insulating material such as a hot metal, molten steel, slag, glass, and semiconductors in various fluid states without being in contact therewith, and an apparatus therefor.

2. Description of the Prior Art

In the past the following methods and combination thereof have been used to analyze molten substances.

(1) Analysis of a sample left at rest in a closed vessel such as a crucible.

(2) Analysis of a sample collected from a flow of a molten substance.

(3) Analysis of the flow of the molten substance by immersing a portion of an excitation source or of a measuring system in the flow.

However, it is difficult to adapt the method of analyzing the sample left at rest in the closed vessel for use during a manufacturing process. Furthermore, the methods of collecting the sample from the flow and immersing the analytical equipment in the flow of the molten substance have been disadvantageous in that the flow of the substance to be measured is disturbed and contaminated.

SUMMARY OF THE INVENTION

The present invention has been developed to obviate the above-described disadvantages of the prior art and contemplates an on-line analysis of the constituents of a fluid metal or insulating substance is to be conducted without contacting the fluid. An object of the present invention is to conduct a continuous on-line analysis of constituents of a substance to be measured, with an excitation source and a measuring system not being in contact with the substance by a method wherein the molten substance to be measured in the fluid state is irradiated by a high output pulse laser beam and an emission spectrum obtained then is spectrally separated.

There have been several cases where this laser emission analysis is applied to the molten substances. However, all of these cases involve analysis of a sample left at rest in a closed vessel such as a crucible, and do not relate to the on-line analysis during a manufacturing process where a molten substance is in a fluid state and the surface of the fluid is moved in the vertical direction.

The present invention relates to an on-line analysis in the manufacturing process where the substance to be measured continuously flows in the molten conditions, and is based on a basic method of a laser emission spectroscopical analysis. According to the method of laser emission spectroscopical analysis, a powerful pulse-shaped laser beam is focused onto the surface of the substance to be measured to cause a surface layer of the substance to be measured to evaporate at a moment, a light is generated from the substance by the excitation of the laser beam, and the light generated is spectrally separated, to thereby conduct an analysis of the constituents. Consequently, there is no need to bring the substance to be measured in contact with a laser system and a spectroscope system.

Now, in practically applying this method of analysis to an analysis on the site, the influence of the vertical movement of the substance to be measured constitutes a major problem. To study the effects of vertical movements of the substance to be measured, the inventors of the present invention used the apparatus shown in FIG. 1. As the laser, an infrared pulse laser having a pulse width of 15 nanosecond, an output of 2 joule and a wavelength of 1.06 micrometer was used.

Description will now be given of FIG. 1. A laser beam generated by a laser oscillator 1 is diverted downwardly by a prism 2, and focused by focusing lens 3 onto the surface of a substance 4 to be measured. Here, the substance 4 to be measured is, an Fe-0.3% Mn alloy which was melted in a Tanmann-furnace 5. At this time, to suppress production of an oxide layer on the surface of the substance 4 to be measured, argon gas was blown in through an argon gas introduction portion 6 and released through an argon gas discharge portion 7 to the outside of the system. The light generated by the laser beam is introduced to a spectroscope 10 by a light introduction system consisting of a concave mirror 8, plane mirrors 9a and 9b. In the spectroscope 10, the wavelength separation is conducted by an ordinary method, and intensities of 271.4 nanometer wavelength Fe spectrum and 293.3 nanometer wavelength Mn spectrum are measured by two light detectors 11. To change the distance between the substance 4 to be measured and the laser spectroscope optical system, the Tanmann-furnace 5 is mounted on a lift 12 and the entire melting furnace is moved in the vertical direction. To avoid disturbing the flow of argon gas, a fitting 13 is interposed between the light introducing system and the Tanmann-furnace 5. As the focusing lenses 3, focusing lenses of five types having focal lengths of 20, 50, 100, 150 and 200 centimeters, respectively, are used, being exchanged from one to another. When the focusing lenses 3 are exchanged, the radius of the concave mirror 8 is selected and the angle of the plane mirrors 9a and 9b is adjusted such that the light generated, when the surface of the substance to be measured was at its focus, forms its image at an inlet slit 14 of the spectroscope. FIG. 2 shows the intensities of Fe and Mn spectra by the vertical movement of the substance 4 to be measured and a change in the ratio therebetween when a focusing lens having a focal length of 100 centimeter is used. As the surface of the substance 4 to be measured is shifted from the focus of the focusing lens 3, the intensity of the spectrum is progressively decreased. However, the intensity ratio between the spectra used in the analysis is not varied even if the surface of the substance is shifted from the focus of the focusing lens 3 by 5 centimeter in the vertical direction. Measurements similar to the above were conducted with the focusing lenses 3 being exchanged, and the results of the measurements are put together and shown in FIG. 3. If the relationship of a distance L between the focusing lens 3 and the surface of the substance 4 to be measured with a focal length f of the focusing lens 3 given by the following formula, $$0.95f \leq L \leq 1.05f \tag{1}$$

then, it was found that the intensity ratio between the spectra was constant and a stable analyzed value was obtainable in spite of the vertical movement of the substance to be measured.

Further, when the substance 4 to be measured is an insulating substance such as $SiO_2$—$Al_2O_3$ and measurements similar to that shown in FIG. 2 are conducted on the line spectra of Si (288.2 nanometer wavelength) and Al (309.3 nanometer wavelength), similar results are obtained. Specifically, FIG. 4 shows the results. In this case also, even if the surface of the substance to be measured is shifted from the focus of the focusing lens 3 by 5 centimeters, the intensity ratio between the spectra is substantially constant. Further, the results of measurements conducted, with the focusing lenses 3 being exchanged from one to another, are substantially equal to that shown in FIG. 3. It has been determined that, the surface of the substance to be measured is not subjected to the influence of the vertical movement of the surface of the substance to be measured if and only if the above formula (1) is satisfied.

The present invention is based on the above-described knowledge and the technical gist thereof resides in a method of continuously analyzing a fluidized body by laser and an apparatus therefor, wherein a focusing lens having a focal length f is provided at a position spaced a distance L apart from the surface of the substance to be measured in the fluid state, control is effected such that the relationship between L and f can satisfy a formula $$0.95f \leq L \leq 1.05f,$$

and an emission of a high power pulse laser, which has irradiated the surface of the substance to be measured, is analyzed spectroscopically.

According to the present invention, even in a manufacturing process where the substance to be measured continuously flows and the vertical movement of the surface of the substance is unavoidable, a laser spectroscope system is provided at a position where the above-mentioned formula (1) is satisfied and a focusing lens 3 having a suitable focal length is selected, so that a stable laser emission spectroscopical analysis can be achieved. Use of focusing lenses having focal lengths 100 to 200 centimeter makes it possible to tolerate vertical movements of the surface of the substance to be measured which range from 10 to 20 centimeters. A portion of an ordinary manufacturing process, where the width of variations in the vertical direction is restricted to the above-mentioned range, may be found and the variations in the movement of the surface of the substance to be measured may be controlled to within the above-mentioned range, so that the present invention can be easily employed. This control may for example be achieved by improving the manufacturing process, specially preparing a runner or the like for constantly satisfying the above-mentioned formula (1) and controlling the runner, or by controlling an inclination of the melting furnace, so that a flow of the substance to be measured, which flows out of the melting furnace, may satisfy the above-mentioned formula (1).

In working the present invention, a variation range of the vertical movement of the surface of the substance to be measured at a position where the apparatus is installed is measured by a suitable method. If a focusing lens having a focal length at least ten times the variation width, then the formula (1) is constantly established and necessity of control of the distance between the substance to be measured and the focusing lens is eliminated. Furthermore, a method wherein the variation range of the vertical movement of the surface of the substance to be measured is less than one-tenth the focal length of the focusing lens may be used.

Subsequently, the light introducing system is adjusted such that the light emitted from the surface of the substance to be measured forms an image at the inlet slit of the spectroscope. As the laser, an infrared pulse laser is suitable, however, a ruby laser capable of obtaining a visible beam may be adopted. Well known methods are used to spectrally separate the light emitted by the irradiation of laser and to measure the intensity of a specified spectrum.

When other materials such as an oxide layer or other obstacle are present on the surface of the substance to be measured, measures such as blowing argon gas or nitrogen gas onto the materials to remove the oxide layer or using an obstacle to separate the materials from the substance to be measured, are provided so that the laser beam can directly irradiate the substance to be measured.

According to the present invention, substances in a fluid state can be analyzed on-line with high accuracy by use of a laser and the accuracies in the process control and the quality control on line are improved to a considerable extent.

BRIEF DESCRIPTION OF THE DRAWINGS

The exact nature of this invention, as well as other objects and advantages thereof, will be readily apparent from consideration of the following specification relating to the accompanying drawings, in which like reference characters designate the same or similar parts throughout the figures thereof and wherein:

FIG. 5 is a side view showing an apparatus embodying the present invention on an iron runner.

DETAILED DESCRIPTION OF THE INVENTION

Figure 1:
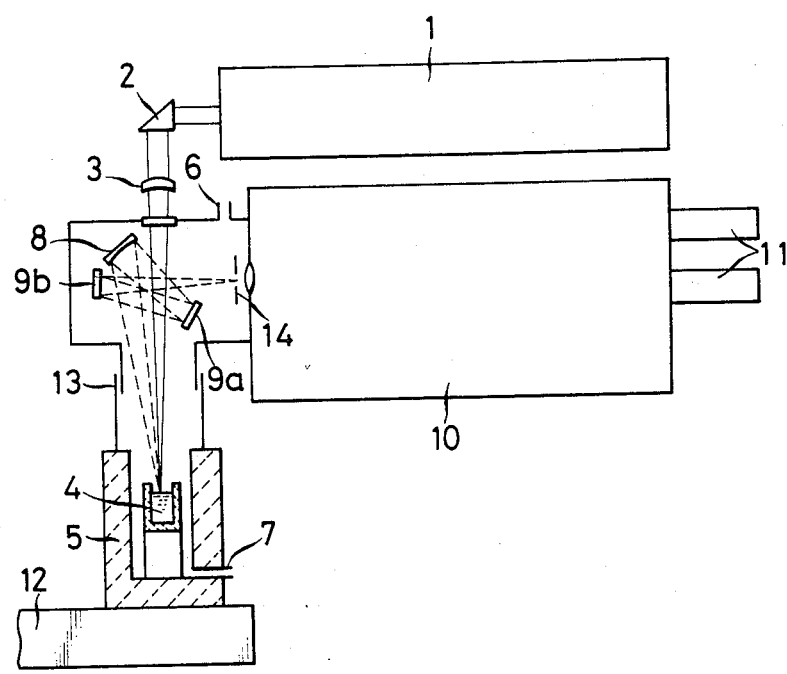
FIG. 1 is a schematic side view showing the apparatus for laser spectroscopical analysis, which was used to study the effect of vertical movement of the surface of the substance to be measured.
Figure 2:
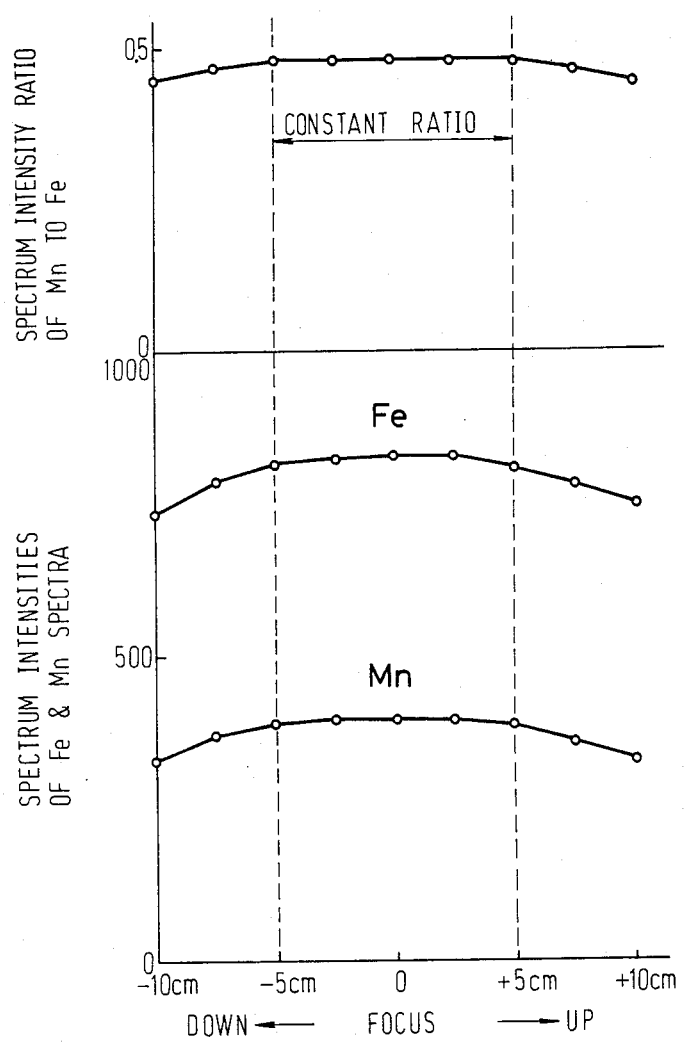
FIG. 2 is a graphic chart showing the changes in the intensities of spectra due to vertical movements of the surface of Fe-0.3% Mn.
Figure 3:
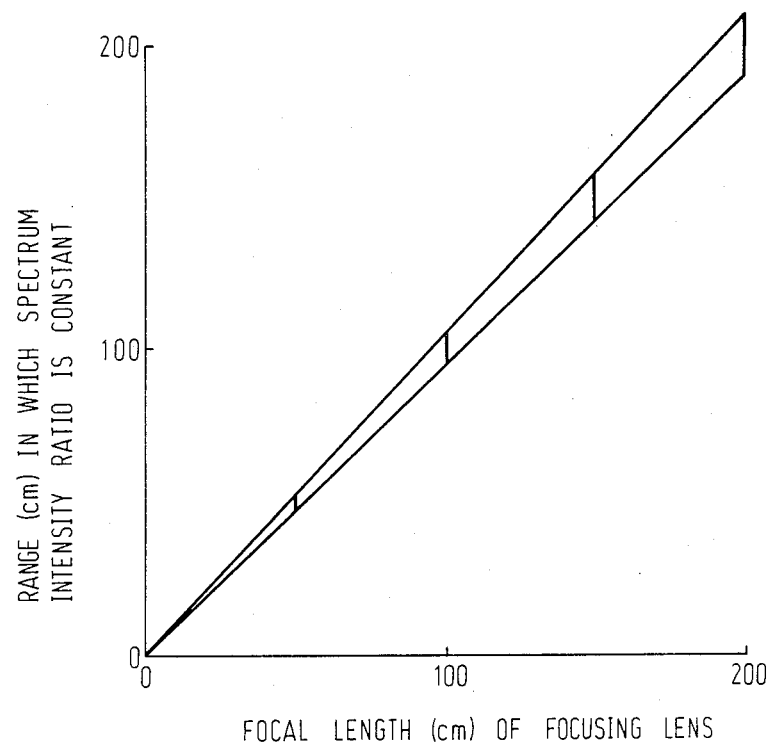
FIG. 3 is a graphic chart showing the range where the intensity ratio of spectra becomes constant.
Figure 4:
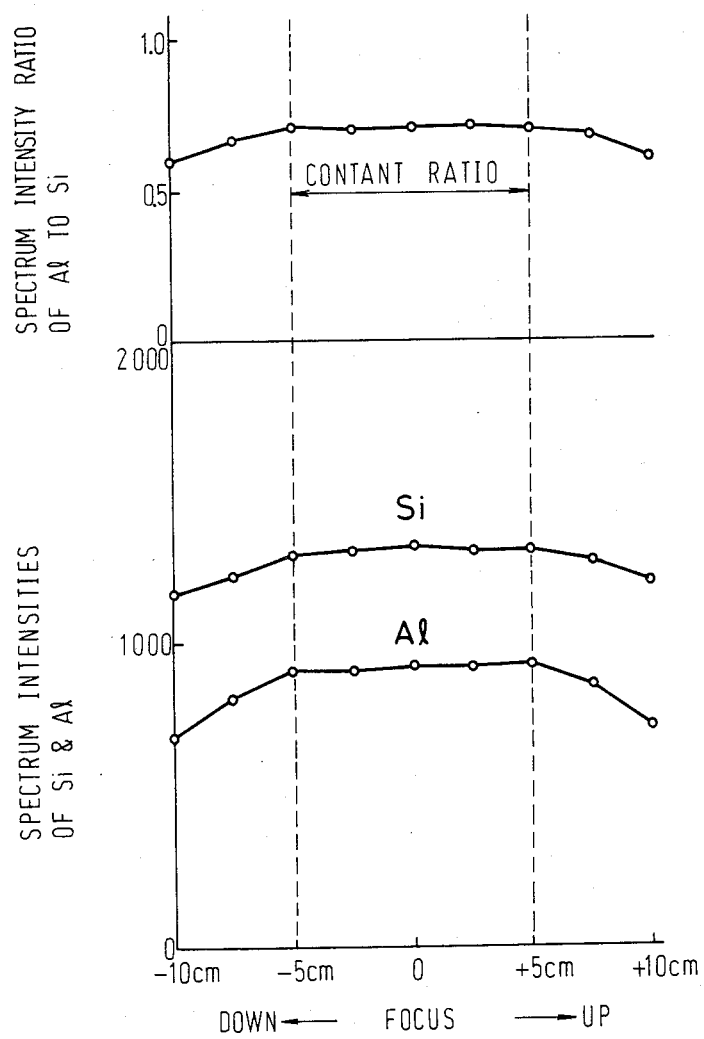
FIG. 4 is a graphic chart showing the changes in the intensities of spectra due to the vertical movements of the surface of $SiO_2$—$Al_2O_3$.

Detailed description will hereunder be given of the embodiment of the present invention with reference to the drawings.

FIG. 5 is a side view showing the apparatus embodying the present invention. The substance 4 to be measured is hot metal flowing through an iron through of a blast furnace. Normally, slag is mounted on the surface of hot metal. The laser spectroscope is provided at a position, where the slag had been just removed by means of a skimmer. As the laser, an infrared ray pulse laser having a pulse width of 15 nanosecond and an output of 2 joule is used. The laser oscillator 1 and the spectroscope 10 are fixed onto an analytical bed 15. The laser beam is vertically diverted by the prism 2 in the direction of the substance to be measured and focused by the focusing lens 3. The maximum vertical movement of the surface of hot metal at this analytical point is 10 centimeters accordingly focusing lens 3, having a focal length at least ten times tHe maximum vertical movement, i.e., 100 centimeters or more should be used. In the illustrated embodiment, a lens having a focal length of 170 centimeter is used so that the light introducing system and the conponents are not subjected to the radiant heat of the hot metal to an excessive extent. The light emitted by the irradiation of laser is adopted to form its image at the inlet slit 14 of the spectroscope by the light introducing system consisting by the concave mirror 8, and the plane mirrors 9a and 9b. To prevent this light introducing system from being contaminated by gases and dust, argon gas is blown in through the argon gas introduction portion 6. Further, to ensure the prevention of the contamination, an argon gunning pipe 16 was mounted to the lower portion of the light introducing system, and argon gas was further blown in through an additional argon gas blown in portion 17. The spectroscope 10 spectrally separates the light by use of a diffraction grating of 2400 line/mm at a focal length of 200 centimeter and the spectrum intensity is detected by a photomultiplier tube 18. Table 1 shows the elements analyzed, the wavelengths of spectra and the results of analysis. The results of using the conventional method, in which the samples are collected, left at rest in crucibles and analyzed, are also shown in this table. The results of analysis according to the present invention well coincide with those obtained by the conventional method.

TABLE 1

| Element | Wavelength nanometer | Results of analysis (%) | |
|---|---|---|---|
| | | Present method | Conventional method |
| Si | 212.4 | 0.40 | 0.37 |
| Mn | 293.3 | 0.39 | 0.44 |
| Cr | 267.7 | 0.021 | 0.023 |
| Ni | 231.6 | 0.018 | 0.016 |

What is claimed is:

1. A method of performing continuous on-line laser emission spectroscopic analysis on a flowing fluid sample, which includes a vertically moving surface, comprising the steps of:
   providing a focusing lens having a focal length f at a fixed position spaced a varying distance L from the vertically moving surface of the flowing fluid sample of the substance to be measured;
   controlling the relationship between L and f such that the formula:

$$0.95f \leqq L \leqq 1.05f$$

is constantly satisfied; and
   spectroscopically analyzing the light emitted by said substance to be measured when said substance is irradiated by a high power pulse laser.

2. A method of continuously analyzing a flowing fluid sample body by laser as set forth in claim 1, wherein said pulse laser is an infrared ray pulse laser.

3. A method of performing continuous on-line laser emission spectroscopic analysis on a flowing fluid sample as set forth in claim 1, wherein materials other than the substance to be measured which are present on the surface of said substance to be measured are blown away by an inert gas.

4. A method of performing continuous on-line laser emission spectroscopic analysis on a flowing fluid sample as set forth in claim 1, wherein materials other than the substance to be measured which are present on the surface of said substance to be measured are separated from said substance by an obstacle.

5. An apparatus for performing continuous on-line laser emission spectroscopic analysis on a flowing fluid sample having a surface which moves in the vertical direction, comprising:
   a laser oscillating means for generating a high output pulse laser;
   a focusing lens, which is provided at a fixed position a varying distance L from the vertically moving surface of the flowing fluid sample of the substance to be measured, such that the relationship between L and the focal length f of said lens constantly satisifies the formula:

$$0.95f \leqq L \leqq 1.05f,$$

wherein the focal length f is at least ten times as large as the range of vertical movement of the surface of said substance to be measured, for focusing the laser generated by said laser oscillating means onto the surface of said flowing fluid sample of the substance to be measured; and
   spectral separating means for analyzing spectroscopically the light emitted from the surface of said substance to be measured.

6. An apparatus for performing continuous on-line laser emission spectroscopic analysis on a flowing fluid sample by laser as set forth in claim 5, wherein an inert gas is blown into a light introducing system for introducing said emitted light into said spectrally separating means.

7. An apparatus for performing continuous on-line laser emission spectroscopic analysis on a flowing fluid sample which includes a vertically moving surface, comprising:
   a laser oscillating means for generating a high output pulse laser;
   a focusing lens, which has a focal length f and is provided at a fixed position spaced a varying distance L from the vertically moving surface of the flowing fluid sample of the substance to be measured for focusing the laser generated by said laser ocsillatng means onto a surface of the substance to be measured; and
   means for controlling the distance L such that the relationship between L and f can constantly satisfy the formula:

$$0.95f \leqq L \leqq 1.05f;$$

and
   spectral separating means for analyzing spectroscopically the light emitted from the surface of said substance to be measured.

8. An apparatus for performing continuous on-line laser emission spectroscopic analysis on a flowing fluid sample by laser as set forth in claim 7, wherein said means for controlling L is a runner through which said substance to be measured flows.

9. An apparatus for performing continuous on-line laser emission spectroscopic analysis on a flowing fluid sample by laser as set forth in claim 7, wherein said means for controlling L is one for controlling the inclination of a melting furnace, out of which said substance to be measured flows.

* * * * *